United States Patent [19]

Stroech et al.

[11] Patent Number: 4,888,048
[45] Date of Patent: Dec. 19, 1989

[54] FUNGICIDAL AND PLANT GROWTH-REGULATING AZOLYL-TETRAHYDROPYRAN DERIVATIVES

[75] Inventors: Klaus Stroech, Solingen; Monika Frie, Odenthal; Klaus Böckmann, Wuppertal; Klaus Lürssen, Bergisch-Gladbach; Stefan Dutzmann, Duesseldorf, all of Fed. Rep. of Germany

[73] Assignee: Bayer Aktiengesellschaft, Leverkusen, Fed. Rep. of Germany

[21] Appl. No.: 213,877

[22] Filed: Jun. 30, 1988

[30] Foreign Application Priority Data

Jul. 4, 1987 [DE] Fed. Rep. of Germany ....... 3722133

[51] Int. Cl.$^4$ .................. C07D 405/12; C07D 249/12; A01N 43/653; A01N 43/50
[52] U.S. Cl. ........................................ 71/92; 71/76; 514/184; 514/383; 514/397; 548/101; 548/262; 548/336
[58] Field of Search ...................... 71/92, 76; 514/184, 514/383, 397; 548/262, 101, 336

[56] References Cited

FOREIGN PATENT DOCUMENTS 0040345 11/1981 European Pat. Off. .
0061835 10/1982 European Pat. Off. .
0180136  5/1986 European Pat. Off. .
2711950  9/1977 Fed. Rep. of Germany .

OTHER PUBLICATIONS

Kawamoto et al., "Synthesis and antifungal, etc.", CA 106: 176250c (1987).

Rentzeal et al., "Tetrahydropyan-2-yl, etc.", CA 104: 202308h (1986).

Primary Examiner—Glennon H. Hollrah
Assistant Examiner—Patricia L. Morris
Attorney, Agent, or Firm—Sprung Horn Kramer & Woods

[57] ABSTRACT

Fungicidal and plant growth-regulating azolyltetrahydropyran derivatives of the formula

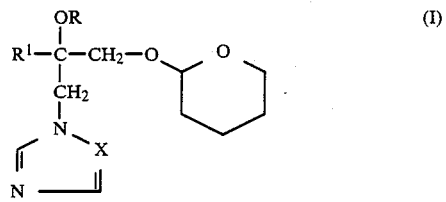

in which
R represents hydrogen, alkyl or acyl,
R$^1$ represents optionally substituted alkyl, optionally substituted cycloalkyl or optionally substituted aryl and
X represents nitrogen or a CH group,
and addition products thereof with acids and metal salts. Intermediates of the formula

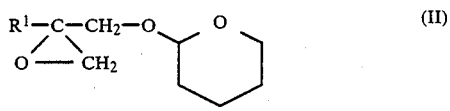

are also new.

11 Claims, No Drawings

FUNGICIDAL AND PLANT GROWTH-REGULATING AZOLYL-TETRAHYDROPYRAN DERIVATIVES

The present invention relates to new azolyl-tetrahydropyran derivatives, several processes for their preparation and their use as fungicides and plant growth regulators.

It is already known that certain azolyl-methyl-cyclopropyl-tetrahydropyran derivatives have fungicidal and plant growth-regulating properties (compare EP-OS No. 0,180,136). Thus, for example, 1,-(4-chlorophenyl)-1-(1-[2-(tetrahydro-2H-pyran-2-yl-oxy)-ethylthio]-1-cyclopropyl)-2-(1,2,4-triazol-1-yl)-1-ethanol can be used for combating fungi and for regulating plant growth. The action of this substance is good; however, it leaves something to be desired in some cases when low amounts are applied.

New azolyl-tetrahydropyran derivatives of the formula

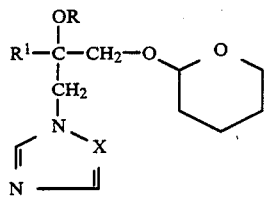

(I)

in which

R represents hydrogen, alkyl or acyl,

R$^1$ represents optionally substituted alkyl, optionally substituted cycloalkyl or optionally substituted aryl and X represents nitrogen or a CH group, and acid addition salts and metal salt complexes thereof, have now been found.

The substances according to the invention contain an asymmetrically substituted carbon atom. They can therefore be obtained in optical isomer forms. The present invention relates both to the individual isomers and to mixtures thereof.

It has furthermore been found that azolyl-tetrahydropyran derivatives of the formula (I) and acid addition salts and metal salt complexes thereof are obtained by a process in which (a) oxiranes of the formula

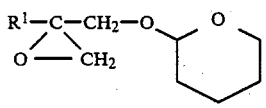

(II)

in which R$^1$ has the abovementioned meaning, are reacted with azoles of the formula

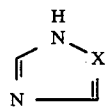

(III)

in which X has the abovementioned meaning, if appropriate in the presence of an acid-binding agent and in the presence of a diluent, or (b) azolyl-tetrahydropyran derivatives of the formula

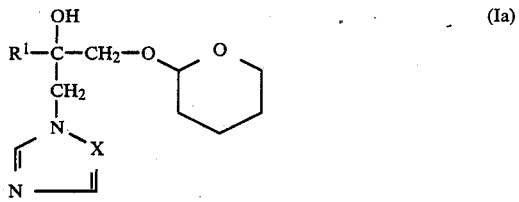

(Ia)

in which R$^1$ and X have the abovementioned meaning, are reacted with strong bases in the presence of a diluent and the alcoholates thereby formed, of the formula

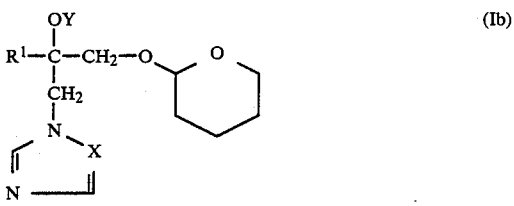

(Ib)

in which

R$^1$ and X have the abovementioned meaning and

Y represents a cationic radical of a base, are reacted with halogen compounds of the formula

R$^2$-Hal (IV)

in which

R$^2$ represents alkyl or acyl and

Hal represents halogen, in the presence of a diluent and if appropriate in the presence of an acid-binding agent, and, if appropriate, an acid or a metal salt is then added onto the compounds of the formula (I) thus obtained.

Finally, it has been found that the new azolyltetrahydropyran derivatives of the formula (I) and acid addition salts and metal salt complexes thereof have powerful fungicidal and plant growth-regulating properties.

Surprisingly, the substances according to the invention are distinguished by a better fungicidal and plant growth-regulating activity than the structurally similar already known compounds of the same type of action.

Formula (I) provides a general definition of the azolyl-tetrahydropyran derivatives according to the invention. Preferably, in this formula, R represents hydrogen, alkyl with 1 to 6 carbon atoms or alkylcarbonyl with 1 to 6 carbon atoms in the alkyl group, R$^1$ represents straight-chain or branched alkyl with 1 to 6 carbon atoms, or represents cycloalkyl which has 3 to 8 carbon atoms in the cycloalkyl part and is optionally substituted by 1 to 3 identical or different substituents from the group comprising alkyl with 1 to 4 carbon atoms and/or halogen, or represents the grouping

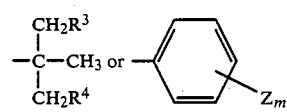

wherein $R^3$ represents hydrogen, halogen or alkoxy with 1 to 4 carbon atoms, $R^4$ represents halogen or alkoxy with 1 to 4 carbon atoms, Z represents halogen, alkyl with 1 to 4 carbon atoms, alkoxy with 1 to 4 carbon atoms, alkylthio with 1 to 4 carbon atoms, halogenoalkyl with 1 or 2 carbon atoms and 1 to 5 halogen atoms, halogenoalkoxy with 1 or 2 carbon atoms and 1 to 5 halogen atoms, halogenoalkylthio with 1 or 2 carbon atoms and 1 to 5 halogen atoms, or phenyl which is optionally substituted by alkyl with 1 or 2 carbon atoms and/or halogen, or represents phenoxy which is optionally substituted by alkyl with 1 or 2 carbon atoms and/or halogen and m represents the number 0, 1, 2 or 3, and X represents nitrogen or a CH group.

Particularly preferred azolyl-tetrahydropyran derivatives of the formula (I) are those in which R represents hydrogen, methyl, ethyl, n-propyl, isopropyl, n-butyl, isobutyl, methylcarbonyl, ethylcarbonyl, n-propylcarbonyl, isopropylcarbonyl, n-butylcarbonyl or isobutylcarbonyl, $R^1$ represents methyl, ethyl, n-propyl, isopropyl, n-butyl, isobutyl, sec.-butyl or tert.-butyl, or represents cycloalkyl which has 3 to 7 carbon atoms in the cycloalkyl part and is optionally substituted by one to three identical or different substituents from the group comprising methyl, ethyl, fluorine and/or chlorine, or represents the grouping

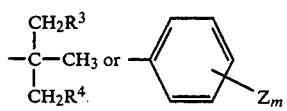

wherein $R^3$ represents hydrogen, fluorine, chlorine, bromine, methoxy or ethoxy, $R^4$ represents fluorine, chlorine, bromine, methoxy or ethoxy, Z represents fluorine, chlorine, bromine, methyl, ethyl, isopropyl, tert.-butyl, methoxy, methylthio, trifluoromethyl, trifluoromethoxy, trifluoromethylthio, phenyl which is optionally substituted by fluorine, chlorine and/or methyl or phenoxy which is optionally substituted by fluorine, chlorine and/or methyl and m represents the number 0, 1, 2 or 3, and X represents nitrogen or a CH group.

If m represents the number 2 or 3, the radicals representing Z can be identical or different. Addition products of acids and of those azolyltetrahydropyran derivatives of the formula (I) in which R, $R^1$ and X have the meanings which have already been mentioned as preferred for these radicals are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid, 1,5-naphthalenedisulphonic acid or camphorsulphonic acid.

Addition products of salts of metals of main groups II to IV and sub-groups I and II and IV to VIII of the Periodic Table of the elements and those azolyltetrahydropyran derivatives of the formula (I) in which R, $R^1$ and X have the meanings which have already been mentioned as preferred for these radicals are also preferred compounds according to the invention.

Salts of copper, zinc, manganese, magnesium, tin, iron and nickel are particularly preferred here. Possible anions of these salts are those which are derived from those acids which lead to physiologically tolerated addition products.

Particularly preferred acids of this type are, in this connection, the hydrogen halide acids, such as, for example, hydrochloric acid and hydrobromic acid, and furthermore phosphoric acid, nitric acid and sulphuric acid.

Examples which may be mentioned of azolyl-tetrahydropyran derivatives of the formula (I) are the substances listed in the following table.

TABLE 1

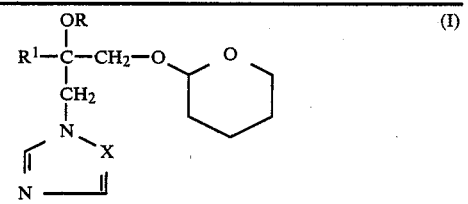

| $R^1$ | R | X |
|---|---|---|
| CH$_3$ | H | N |
| C$_2$H$_5$ | H | N |
| n-C$_3$H$_7$ | H | N |
| n-C$_4$H$_9$ | H | N |
| (CH$_3$)$_3$C | CH$_3$ | N |
| (CH$_3$)$_3$C | —CO—CH$_3$ | N |
| CH$_3$—C(CH$_2$Cl)(CH$_3$)— | H | N |
| CH$_3$—C(CH$_2$Cl)(CH$_2$Cl)— | H | N |
| CH$_3$—C(CH$_2$F)(CH$_3$)— | H | N |
| CH$_3$—C(CH$_2$F)(CH$_2$F)— | H | N |
| 4-F-C$_6$H$_4$— | H | N |
| 2,4-F$_2$-C$_6$H$_3$— | H | N |

TABLE 1-continued $$\text{(I)}$$

Structure: R¹–C(OR)(CH₂–O–tetrahydropyran-2-yl)–CH₂–N(X=N, CH=N) (triazole/imidazole ring)

| R¹ | R | X |
|---|---|---|
| 4-CH₃-C₆H₄- | H | N |
| 4-CH₃O-C₆H₄- | H | N |
| 4-CH₃S-C₆H₄- | H | N |
| 4-CF₃-C₆H₄- | H | N |
| 2,4,5-Cl₃-C₆H₂- | H | N |
| 4-biphenylyl- | H | N |
| C₆H₅- | H | N |
| 1-chlorocyclopropyl- | H | N |
| 4-phenoxyphenyl- | H | N |
| 2-Cl-4-CH₃-C₆H₃- | H | N |
| cyclopropyl- | H | N |
| 1-methylcyclopropyl- | H | N |
| cyclopentyl- | H | N |
| 1-methylcyclohexyl- | H | N |
| (CH₃)₃C | C₂H₅ | N |
| (CH₃)₃C | CO—C₂H₅ | N |
| (CH₃)₃C | CH₃ | CH |
| (CH₃)₃C | C₂H₅ | CH |
| (CH₃)₃C | CO—CH₃ | CH |
| (CH₃)₃C | CO—C₂H₅ | CH |
| 4-CF₃O-C₆H₄- | H | N |
| 4-CF₃S-C₆H₄- | H | N |
| 4'-chloro-4-biphenylyl- | H | N |

If 2-tert.-butyl-2-(tetrahydro-2H-pyran-2-yloxymethyl)-oxirane and 1,2,4-triazole are used as starting substances, the course of process (a) according to the invention can be illustrated by the following equation:

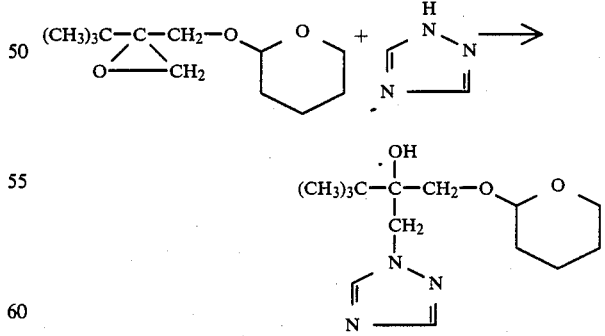

If 2-tert.-butyl-1-(tetrahydro-2H-pyran-2-yloxy)-3-(1,2,4-triazol-1-yl)-propan-2-ol and sodium hydride are used as starting substances and iodomethane is used as reaction component, the course of process (b) according to the invention can be illustrated by the following equation:

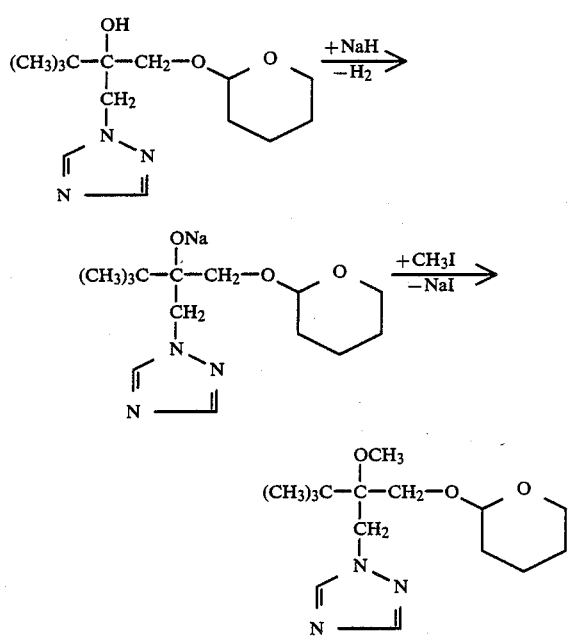

Formula II provides a general definition of the oxiranes required as starting substances in process (a) according to the invention. In this formula, $R^1$ preferably has those meanings which have already been mentioned as preferred for this radical in connection with the description of the substances of the formula (I) according to the invention.

The oxiranes of the formula (II) are not yet known. They can be prepared by a process in which (c) ketones of the formula

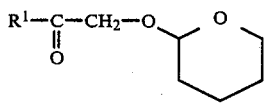

(V)

in which $R^1$ has the abovementioned meaning, (α) are reacted with dimethyloxosulphonium methylide of the formula

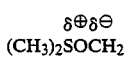

(VI)

or (β) are reacted with dimethylsulphonium methylide of the formula

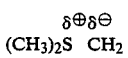

(VII)

in the presence of a diluent.

The ketones of the formula (V) required as starting substances in process (c) are known in some cases (compare Chem. Soc. Perkin Trans. I 1985, 283–287). They can be prepared by a process in which (d) hydroxyketones of the formula

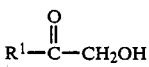

(VIII)

in which $R^1$ has the abovementioned meaning, are reacted with 3,4-dihydro-2H-pyran of the formula

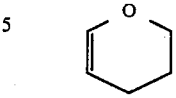

(IX)

in the presence of a catalyst and if appropriate in the presence of a diluent.

The compounds of the formulae (VIII) and (IX) required as starting substances in process (d) are known or can be prepared by methods which are known in principle.

Possible catalysts in carrying out process (d) are all the reaction accelerators customary for such reactions. Reaction accelerators which can preferably be used are acids, such as, for example, hydrochloric acid or sulphuric acid.

Process (d), like processes (a) to (c), is in general carried out under normal pressure. However, it is in each case also possible to carry out the process under increased or reduced pressure.

Process (d) is in general carried out without using an additional diluent. However, it is also possible to carry out the process in the presence of an inert organic solvent. Solvents which can preferably be used here are diethyl ether, dioxane, tetrahydrofuran, toluene, methylene chloride or chloroform.

The reaction temperatures can be varied within a substantial range in carrying out process (d). The reaction is in general carried out at temperatures between 0° C. and 100° C., preferably between 0° C. and 60° C.

In carrying out process (d), in general 1 to 3 mols of 3,4-dihydro-2H-pyran of the formula (IX) and a small amount of catalyst are employed per mol of hydroxyketone of the formula (VIII). Working up is carried out by customary methods.

The dimethyl-oxo-sulphonium methylide of the formula (VI) required as the reaction component in process (c) is known (compare J. Am. Chem. Soc. 87, 1363–1364 (965)). It is processed in the above-mentioned reaction in a freshly prepared state, where it is produced in situ by reacting trimethyloxosulphonium iodide with sodium hydride, sodium amide, potassium tert.-butylate or sodium methylate in the presence of a diluent.

The dimethylsulphonium methylide of the formula (VII) which is also suitable as a reaction component in process (c) is also known compare Heterocycles 8, 397 (1977)). It is likewise used in the above-mentioned reaction in a freshly prepared state, where it is produced in situ, for example from a trimethylsulphonium halide or trimethylsulphonium methylsulphate in the presence of a strong base, such as, for example, sodium hydride, sodium amide, sodium methylate, potassium tert.-butylate or potassium hydroxide, in the presence of a diluent, such as tert.butanol or dimethylsulphoxide.

Possible diluents in carrying out process (c) are inert organic solvents. Solvents which can preferably be used are alcohols, such as tert.-butanol, ethers, such as tetrahydrofuran or dioxane, and furthermore aliphatic and aromatic hydrocarbons, such as benzene, toluene or xylene, as well as strongly polar solvents, such as dimethylsulphoxide or acetonitrile.

The reaction temperatures can be varied within a substantial range in carrying out process (c). The reaction is in general carried out between 0° C. and 100° C., preferably between 10° C. and 60° C.

In carrying out process (c), in general 1 to 3 mols of dimethyloxosulphonium methylide of the formula (VI) or dimethylsulphonium methylide of the formula (VII) are employed per mol of ketone of the formula (V). The oxiranes of the formula (II) are isolated by customary methods.

The azoles of the formula (III) required as reaction components in carrying out process (a) according to the invention are generally known compounds of organic chemistry.

Possible acid-binding agents in carrying out process (a) according to the invention are all the customary acid acceptors. Acid acceptors which can preferably be used are alkali metal carbonates and bicarbonates, such as sodium carbonate, potassium carbonate or sodium bicarbonate, and furthermore alkali metal hydroxides and alcoholates, such as sodium hydroxide, potassium hydroxide, sodium methylate or potassium tert.-butylate, and also tertiary aliphatic or aromatic amines, such as triethylamine, N,N-dimethyl-benzylamine and pyridine, and also cyclic amines, such as 1,5-diaza-bicyclo[4,3,0]-non-5-ene (DBN), 1,8-diaza-bicyclo[5,4,0]undec-7-ene (DBU) and 1,4-diaza-bicyclo[2,2,2]octane (DABCO).

Possible diluents in carrying out process (a) according to the invention are all customary inert organic solvents.

Solvents which can preferably be used are nitriles, such as, in particular, acetonitrile; aromatic hydrocarbons, such as benzene, toluene and dichlorobenzene; formamides, such as, in particular, dimethylformamide, and hexamethylphosphoric acid triamide.

The reaction temperatures can be varied within a substantial range in carrying out process (a) according to the invention. The reaction is in general carried out at temperatures between 0° C. and 200° C., preferably between 50° C. and 150° C.

In carrying out process (a) according to the invention, 1 to 4 mols of azole of the formula (III) and 1 to 2 mols of base are preferably employed per mol of oxirane of the formula (II). The products are isolated in a customary manner.

The azolyl-tetrahydropyran derivatives of the formula (Ia) required as starting substances for process (b) according to the invention are compounds according to the invention. They are converted into the corresponding alcoholates in a generally known manner, in that they are reacted with suitable strong bases, such as alkali metal amides or hydrides, quaternary ammonium hydroxides or phosphonium hydroxides, in an inert diluent, such as, for example, dioxane, at room temperature. Y in the compounds of the formula (Ib) accordingly preferably represents an alkali metal cation, such as the sodium or potassium cation, or a quaternary ammonium or phosphonium cation.

Formula (IV) provides a general definition of the halogen compounds also required as starting substances in process (b) according to the invention. In this formula, $R^2$ preferably represents those meanings which have already been mentioned for the substituent R in connection with the description of the substances of the formula (I) according to the invention, with the exception of the meaning of hydrogen. Hal preferably represents chlorine or bromine.

The halogen compounds of the formula (IV) are known or can be prepared by methods which are known in principle.

Possible diluents in carrying out process (b) according to the invention are inert organic solvents. These include, preferably, ethers, such as diethyl ether or dioxane; aromatic hydrocarbons, such as benzene; and in individual cases also chlorinated hydrocarbons, such as chloroform, methylene chloride or carbon tetrachloride; and hexamethylphosphoric acid triamide.

Acid-binding agents which can be used in carrying out the second stage of process (b) according to the invention are all the customary acid acceptors.

The reaction temperatures can be varied within a substantial range in carrying out process (b) according to the invention. The reaction is in general carried out between 0° C. and 120° C., preferably between 20° C. and 100° C.

In carrying out process (b) according to the invention, hydroxy compounds of the formula (Ia) are first reacted with strong bases to give the corresponding alcoholates of the formula (Ib). In the subsequent stage, 1 to 2 mols of halogen compound of the formula IV) are preferably employed per mol of an alcoholate of the formula (Ib).

To isolate the end products, the reaction mixture is freed from the solvent, and water and an organic solvent are added to the residue. The organic phase is separated off and worked up and purified in the customary manner.

In a preferred embodiment, a procedure is advantageously followed in which a hydroxy compound of the formula (Ia) is used as the starting substance and this is converted into the alkali metal alcoholate in a suitable organic solvent by means of an alkali metal hydride or alkali metal amide, and the product is immediately reacted with a halogen compound of the formula (IV) without isolation, the compounds of the formula (I) according to the invention being obtained in one operation with the elimination of alkali metal halide.

According to another preferred embodiment, the preparation of the alcohols and the reaction with a halogen compound of the formula (IV) are advantageously carried out in a two-phase system, such as, for example, aqueous sodium hydroxide solution or potassium hydroxide solution/toluene or methylene chloride, with the addition of 0.01–1 mol of a phase-transfer catalyst, such as, for example, ammonium or phosphonium compounds, the reaction of the alcoholates with the halides in the organic phase taking place in the organic phase or at the phase boundary.

The azolyl-tetrahydropyran derivatives of the formula (I) obtainable by the processes according to the invention can be converted into acid addition salts or metal salt complexes.

Those acids which have already been mentioned as preferred acids in connection with the description of the acid addition salts according to the invention are preferably used to prepare acid addition salts of the compounds of the formula (I).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Those salts of metals which have already been mentioned as preferred metal salts in connection with the description of the metal salt complexes according to the invention can preferably be used to prepare metal salt complexes of the compounds of the formula (I).

The metal salt complexes of the compounds of the formula (I) can be obtained in a simple manner by customary processes, thus, for example, by dissolving the metal salt in alcohol, for example ethanol, and adding the solution to compounds of the formula (I). The metal salt complexes can be isolated in a known manner, for example by filtration, and if appropriate purified by recrystallization.

The active compounds according to the invention have a powerful microbicidal action and can be used as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as, for example, Xanthomonas oryzae; Pseudomonas species, such as Pseudomonas lachrymans; Erwinia species, such as Erwinia amylovora; Pythium species, such as Pythium ultimum; Phytophthora species, such as Phytophthora infestans; Pseudoperonospora species, such as Pseudoperonospora humuli or Pseudoperonospora cubense; Plasmopara species, such as Plasmopara viticola; Peronospora species, such as Peronospora pisi or P. brassicae; Erysiphe species, such as Erysiphe graminis; Sphaerotheca species, such as Sphaerotheca fuliginea; Podosphaera species, such as Podosphaera leucotricha; Venturia species, such as Venturia inaequalis; Pyrenophora species, such as Pyrenophora teres or P. graminea; (conidia form: Drechslera, syn: Helminthosporium); Cochliobolus species, such as Cochliobolus sativus; (conidia form: Drechslera, syn: Helminthosporium); Uromyces species, such as Uromyces appendiculatus; Puccinia species, such as Puccinia recondita; Tilletia species, such as Tilletia caries; Ustilago species, such as Ustilago nuda or Ustilago avenae; Pellicularia species, such as Pellicularia sasakii; Pyricularia species, such as Pyricularia oryzae; Fusarium species, such as Fusarium culmorum; Botrytis species, such as Botrytis cinerea; Septoria species, such as Septoria nodorum; Leptosphaeria species, such as Leptosphaeria nodorum; Cercospora species, such as Cercospora canescens; Alternaria species, such as Alternaria brassicae and Pseudocercosporella species, such as Pseudocercosporella herpotrichoides.

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating cereal diseases and rice diseases, such as mildew and rust diseases on cereals, and Pyricularia and Pellicularia on rice.

The active compounds according to the invention furthermore also have plant growth-regulating properties.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sports grounds, on verges, at airports or in fruit orchards. The inhibition of growth of herbaceous and woody plants on verges and in the vicinity of pipelines or overland lines or, quite generally, in areas in which heavy additional growth of plants is undesired, is also of importance.

The use of growth regulators to inhibit the growth in length of cereals is also important. The danger of bending ('lodging') of the plants before harvesting is thereby reduced or completely eliminated. Furthermore, growth regulators can strengthen the stem of cereals, which again counteracts lodging. Use of growth regulators for shortening and strengthening the stem enables larger amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beets' sugar cane, pineapples and citrus fruit or to increase the protein content in soy beans or cereals. Using growth regulators it is also possible, for example, to inhibit the degradation of desired constituents, such as, for example, sugar in sugar beets or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example in the cultivation of tobacco or in the planting of tomatoes.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a desired degree ('thinning out') in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can in many cases improve the coloration of fruit. In addition, concentrating the ripening within a certain period of time is also achievable with the aid of growth regulators. This provides the preconditions for being able to carry out complete mechanical or manual harvesting in a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, resistance of plants to frost, drought or a high salt content in the soil can be induced with growth regulators. Cultivation of plants in regions which are usually unsuitable for this purpose thereby becomes possible.

The active compounds are particularly suitable for inhibiting growth in cereals, rice and soy beans.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and other growth regulators.

The active compounds can be used as such or in the form of their formulations or in the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

When the substances according to the invention are used as fungicides, the amount applied can be varied within a substantial range, depending on the nature of the application. In the treatment of parts of plants, the active compound concentration in the use forms is thus in general between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02%, are required at the place of action.

When the compounds according to the invention are used as plant growth regulators, the amounts applied can be varied within a substantial range. In general, 0.01 to 50 kg, preferably 0.05 to 10 kg of active compound are used per hectare of soil surface.

When the substances according to the invention are used as plant growth regulators, the rule is that the application is carried out within a preferred period of time, the exact definition of which depends on the climatic and vegetative circumstances.

The preparation and use of the active compounds according to the invention can be seen from the following examples.

PREPARATION EXAMPLES

EXAMPLE 1

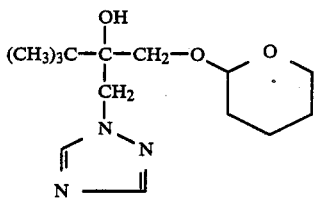
(I-1)

A solution of 160 g (0.75 mol) of 2-tert.-butyl-2-(tetrahydro-2H-pyran-2-yloxymethyl)-oxirane in 180 ml of absolute dimethylformamide is added dropwise to a mixture of 168 g (2.45 mols) of 1,2,4-triazole, 18.2 g (0.16 mol) of potassium tert.-butylate and 350 ml of absolute dimethylformamide at 80° C. under a nitrogen atmosphere. The reaction mixture is stirred at 80° C. for 6 hours and is then concentrated by stripping off the diluent under reduced pressure. The residue which remains is taken up in ethyl acetate and the organic solution formed is washed with water and then dried over sodium sulphate, and concentrated by stripping off the solvent under reduced pressure. The product thus obtained is purified chromatographically over silica gel with chloroform as the mobile phase. 107.3 g (51% of theory) of 2-tert.-butyl-1-(tetrahydro-2H-pyran-2-yloxy)-3-(1,2,4-triazol-1-yl)-propan-2-ol (mixture of diastereomers) are obtained in this manner.

$^1$H-NMR (80 MHz, CDCl$_3$): δ=1.03 and 1.07 (in each case s, together 9H), 1.3 to 1.8 (m, 6H) 2.9 to 3.85 (m, 5H), 4.15 to 4.65 (m, 3H), 7.90 and 7.92 (in each case s, together 1H), 8.17 and 8.25 (in each case s, together 1H).

Preparation of starting substances:

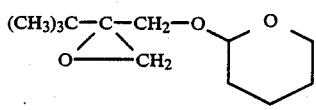
(II-1)

880 ml of absolute dimethylsulphoxide are added dropwise to a mixture of 38.2 g (1.27 mols) of sodium hydride (80% strength) and 271.5 g (1.23 mols) trimethyl-oxosulphonium iodide at 10° C. under a nitrogen atmosphere, with stirring. The mixture is subsequently stirred for a further hour at room temperature and is then cooled to 10° C., and a solution of 219 g (1.1 mols) of 3,3-dimethyl-1-(tetrahydro-2H-pyran-2-yloxy)-butan-2-one in 250 ml of absolute dimethylsulphoxide is added dropwise at this temperature. The reaction mixture is stirred at room temperature for 48 hours and then poured into water. The mixture is extracted with ethyl acetate and the combined organic phases are washed with water, dried over sodium sulphate and concentrated by stripping off the diluent under reduced pressure. 219.4 g (94% of theory) of 2-tert.-butyl-2-(tetrahydro-2H-pyran-2-yloxymethyl) oxirane are obtained in this manner.

$^1$H-NMR (80 MHz, CDCl$_3$): δ=1.0 (s, 9H), 1.3 to 1.8 (m, 6H) 2.65 to 2.9 (m, 2H), 3.35 to 4.15 (m, 4H), 4.5 to 4.65 (m, 1H).

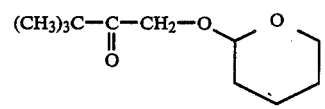
(V-1)

A solution of 162 g (1.4 mols) of 3,3-dimethyl-1-hydroxy-butan-2-one in 62 g (0.74 mol) of 3,4-dihydro-2H-pyran is added dropwise to a mixture of 61 g (0.73 mol) of 3,4-dihydro-2H-pyran and 4 drops of concentrated hydrochloric acid at room temperature, while stirring. The reaction mixture is stirred at room temperature for 12 hours, 400 ml of ethyl acetate are then added, the mixture is washed twice with 5% strength aqueous sodium hydroxide solution and once with water and the organic phase is dried over sodium sulphate and concentrated by stripping off the volatile constituents under reduced pressure. 273.7 g (98% of theory) of 3,3-dimethyl-1-(tetrahydro-2H-pyran-2-yloxy)-butan-2-one remain.

$^1$H-NMR (60 MHz, CDCl$_3$): δ=1.2 (s, 9H), 1.3 to 2.0 (m, 6H), 3.4 to 4.1 (m, 2H), 4.5 (s, 2H), 4.6 and 4.75 (m, 1H).

EXAMPLE 2

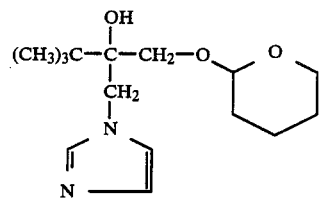
(I-2)

A solution of 59 g (0.28 mol of 2-tert.-butyl-2-(tetrahydro-2H-pyran-2-yloxy-methyl)-oxirane in 100 ml of acetonitrile is added dropwise to a mixture of 119 g 1.75 mol of imidazole, 1 g 9 mols) of potassium tert.-butylate and 500 ml of acetonitrile under a nitrogen atmosphere, the reaction mixture being boiled under reflux. When the addition has ended, the mixture is boiled under reflux for a further 10 hours, the solvent is then stripped off under reduced pressure and the residue which remains is taken up in ethyl acetate. The organic phase is washed with water, dried over sodium sulphate and concentrated under reduced pressure. The product thus obtained is purified chromatographically over silica gel with chloroform as the mobile phase. 56.3 g (72% of theory) of 2-tert.-butyl-3-(imidazol-1-yl)-1-(tetrahydro-2H-pyran-2-yloxy)-propan-2-ol are obtained in this manner in the form of a solid substance of melting point 107° C.

EXAMPLE 3

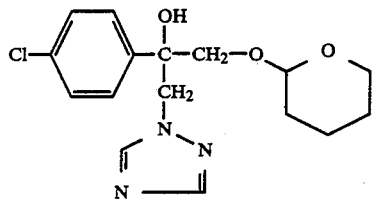

37 g (0.138 mol) of 2-(4-chlorophenyl)-2-(tetrahydro-2H-pyran-2-yl-oxymethyl)-oxirane are added to a mixture of 22.4 g (0.32 mol) of 1,2,4-triazole, 5 g (0.04 mol) of potassium tert.-butylate and 300 ml of dimethylformamide at room temperature, while stirring. After the addition has ended, the reaction mixture is stirred at 80° C. for 12 hours and is then concentrated by stripping off the solvent under reduced pressure. Water is added to the residue which remains, the resulting mixture is extracted three times with methylene chloride and the combined organic phases are dried over magnesium sulphate and concentrated by stripping off the solvent under reduced pressure. The product thus obtained is purified chromatographically on silica gel with methylene chloride/ethyl acetate =4:1 as the mobile phase. 33.5 g (72% of theory) of 2-(4-chlorophenyl)-1-[(tetrahydro-2H-pyran-2-yl)-oxy]-3-(1,2,4-triazol-1-yl)-propan-2-ol are obtained in this manner in the form of pale yellow crystals of melting point 70° C.

Preparation of starting substances:

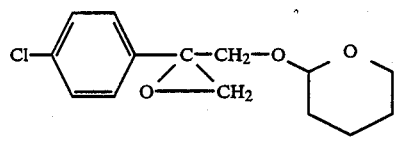

6.3 g (0.21 mol) of sodium hydride (80% strength) are added to a mixture of 42 g (0.19 mol) of trimethylsulphoxonium iodide and 200 ml of dimethylsulphoxide at 15° C. The reaction mixture is stirred at room temperature for 1 hour and a solution of 39 g (0.153 mol) of 1-(4-chlorophenyl)-2-[(tetrahydro-2H-pyran-2-yl)-oxy]-ethan-1-one in 50 ml of dimethylsulphoxide is then added dropwise. The reaction mixture is stirred at 50° C. for 12 hours and then poured into water. The mixture formed is extracted three times with ethyl acetate. The combined organic phases are dried over magnesium sulphate and concentrated by stripping off the solvent under reduced pressure. 37 g (90% of theory) of 2-(4-chlorophenyl)-2-(tetrahydro-2H-pyran-2-yloxymethyl)-oxirane are obtained in this manner in the form of a pale yellow oil which is used for the subsequent synthesis without additional purification.

$R_f$=0.55 (methylene chloride).

IR (film): 2,920, 2,875$^s$ (CH); 1,600$^m$, 1,500$^m$ (C=C) 1,250$^m$ (C-O); 1,120$^s$ (C-O) cm$^{-1}$.

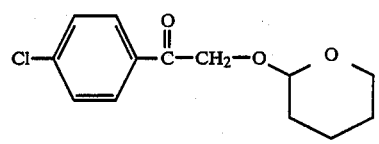

4 drops of concentrated hydrochloric acid are added to a mixture of 26.5 g (0.155 mol) of 4-chloro-ω-hydroxyacetophenone and 45 ml of 3,4-dihydro-2H-pyran and the mixture is stirred at 60° C. for 2 hours. The volatile constituents are then stripped off under reduced pressure. 39 g (99% of theory) of 1-(4-chlorophenyl)-2-[(tetrahydro-2H-pyran-2-yl)-oxy]-ethan-1-one are obtained in this manner in the form of a colorless solid of melting point 57° C.

EXAMPLE 4

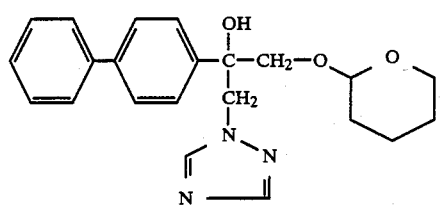

2-(Biphenyl-4-yl)-1-[(tetrahydro-2H-pyran-2-yl)oxy]-3-(1,2,4-triazol-1-yl)-propan-2-ol of the formula (I-4) is also prepared by the method described in Example 3.

Melting point: 78° C.

The compounds mentioned in the following examples are prepared in analogous manner.

EXAMPLE 5

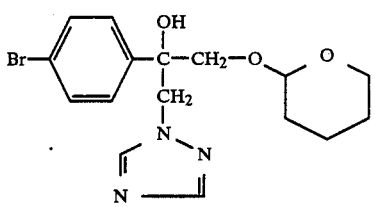

Melting point: 86° C.

EXAMPLE 6

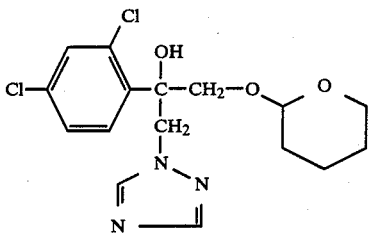

Melting point: 97° C.

The compound shown below was employed as the comparison substance in the following use examples:

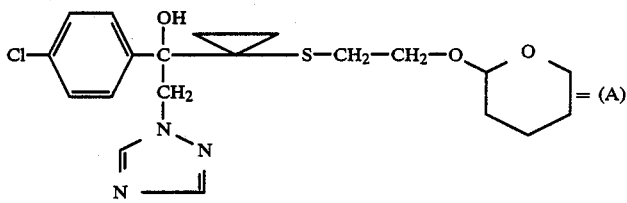

(known from EP-OS 0,180,136).

EXAMPLE A

Growth of barley

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Barley plants are grown in a greenhouse to the 2-leaf stage. In this stage, the plants are sprayed with the preparations of active compound until dripping wet. After 14 days, the additional growth is measured on all plants and the growth in per cent of the additional growth of the control plants is calculated. 100% denotes a growth corresponding to that of the control plants. Values above 100% characterize promotion of growth, while values below 100% indicate inhibition of growth.

In this test, compound (I-1) according to the invention shows a potent growth-inhibiting action, while comparison substance (A) exerts a weak growth-promoting action.

EXAMPLE B

Growth of soy beans

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soy bean plants are grown in a greenhouse until the first secondary leaf has unfolded completely. At this stage, the plants are sprayed with the preparations of active compound until dripping wet. After 14 days, the additional growth is measured on all the plants and the growth in per cent of the additional growth of the control plants is calculated. 100% denotes a growth corresponding to that of the control plants. Values above 100% characterize promotion of growth, while values below 100% indicate inhibition of growth.

In this test, compound (I-1) according to the invention shows a very good growth-inhibiting action.

EXAMPLE C

Growth of rye

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Rye plants are grown in a greenhouse to the 2-leaf stage. At this stage, the plants are sprayed with the preparations of active compound until dripping wet. After 14 days, the additional growth is measured on all plants and the growth in per cent of the additional growth of the control plants is calculated. 100% denotes a growth corresponding to that of the control plants. Values above 100% characterize promotion of growth, while values below 100% indicate inhibition of growth.

In this test, compound (I-1) according to the invention shows a very potent growth-inhibiting action.

EXAMPLE D

Growth of wheat

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Wheat plants are grown in a greenhouse to the 2-leaf stage. At this stage, the plants are sprayed with the preparations of active compound until dripping wet. After 14 days, the additional growth is measured on all plants and the growth in per cent of the additional growth of the control plants is calculated. 100% denotes a growth corresponding to that of the control plants. Values above 100% characterize promotion of growth, while values below 100% indicate inhibition of growth.

In this test, compound (I-1) according to the invention shows a potent growth-inhibiting action.

EXAMPLE E

Puccinia Test (wheat)/protective

Solvent: 100 parts by weight of dimethylformamide
Emulsifier: 0.25 Parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1 strength aqueous agar solution. After the spore suspension has dried on, the plants are sprayed with the preparation of active compound until dew-moist. The plants remain in an incubation cabin at 20° C. and 100 % relative atmospheric humidity for 24 hours.

The plants are placed in a greenhouse at a temperature of about 20° C. and a relative atmospheric humidity of about 80 % in order to promote the development of rust pustules.

Evaluation is carried out 10 days after the inoculation.

In this test, compound (I-3) according to the invention shows a markedly better activity than the comparison substance (A).

It will be appreciated that the instant specification and claims are set forth by way of illustration and not limitation, and that various modifications and changes may be made without departing from the spirit and scope of the present invention.

What is claimed is:

1. An azolyl-tetrahydropyran derivative of the formula

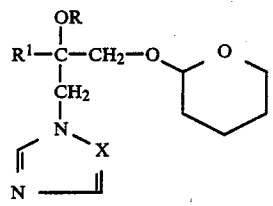

in which
R represents hydrogen, alkyl with 1 to 6 carbon atoms or alkylcarbonyl with 1 to 6 carbon atoms in the alkyl group,
$R^1$ represents straight-chain or branched alkyl with 1 to 6 carbon atoms, or represents cycloalkyl which has 3 to 8 carbon atoms in the cycloalkyl part and is optionally substituted by 1 to 3 identical or different substituents from the group consisting of alkyl with 1 to 4 carbon atoms and halogen, or represents the grouping

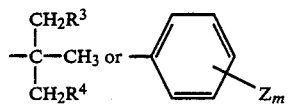

wherein
$R^3$ represents hydrogen, halogen or alkoxy with 1 to 4 carbon atoms,
$R^4$ represents halogen or alkoxy with 1 to 4 carbon atoms,
Z represents halogen, alkyl; with 1 to 4 carbon atoms, alkoxy with 1 to 4 carbon atoms, alkylthio with 1 to 4 carbon atoms, halogenoalkyl with 1 or 2 carbon atoms and 1 to 5 halogen atoms, halogenoalkoxy with 1 to 2 carbon atoms and 1 to 5 halogen atoms, halogenoalkylthio with 1 or 2 carbon atoms and 1 to 5 halogen atoms, or phenyl which is optionally substituted by alkyl with 1 or 2 carbon atoms and/or halogen, or represents phenoxy which is optionally substituted by alkyl with 1 of 2 carbon atoms and/or halogen and
m represents the number 0, 1, 2 or 3, and
x represents nitrogen or a CH group,
or an addition product thereof with an acid or metal salt.

2. A compound or addition product thereof according to claim 1, in which
R represents hydrogen, methyl, ethyl, n-propyl, isopropyl, n-butyl, isobutyl, methylcarbonyl, ethylcarbonyl, n-propylcarbonyl, isopropylcarbonyl, n-butylcarbonyl or isobutylcarbonyl, $R^1$ represents methyl, ethyl, n-propyl, isopropyl, n-butyl, isobutyl, sec.-butyl or tert.-butyl, or represents cycloalkyl which has 3 to 7 carbon atoms in the cycloalkyl part and is optionally substituted by one to three identical or different substituents from the group consisting of methyl, ethyl, fluorine and chlorine, or represents the grouping

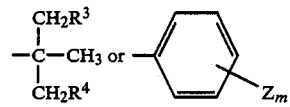

wherein
$R^3$ represents hydrogen, fluorine, chlorine, bromine, methoxy or ethoxy,
$R^4$ represents fluorine, chlorine, bromine, methoxy or ethoxy,
Z represents fluorine, chlorine, bromine, methyl, ethyl, isopropyl, tert.-butyl, methoxy, methylthio, trifluoromethyl, trifluoromethoxy, trifluoromethylthio, phenyl which is optionally substituted by fluorine, chlorine and/or methyl or phenoxy which is optionally substituted by fluorine, chlorine and/or methyl and
m represents the number 0, 1, 2 or 3, and
X represents nitrogen or a CH group.

3. A compound or addition product thereof according to claim 1, in which
R represents hydrogen,
$R^1$ represents cycloalkyl with 3 to 7 carbon atoms optionally substituted by methyl, or represents the grouping

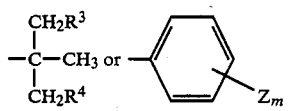

wherein
$R^3$ represents hydrogen, fluorine or chlorine,
$R^4$ represents fluorine or chlorine,
z represents fluorine, chlorine, bromine, methyl, trifluoromethyl or phenyl, and
m represents the number 0, 1 or 2.

4. A compound according to claim 1, wherein such compound is 2-tert.-butyl-1-[(tetrahydro-2H-pyran-2-yl)-oxy]-3-(1,2,4-triazol-1-yl)-propan-2-ol of the formula

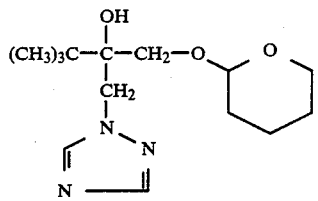

or an addition product thereof with an acid or metal salt.

5. A compound according to claim 1, wherein such compound is 2-(4-chlorophenyl)-1-[(tetrahydro-2H- pyran-2-yl)-oxy]-3-(1,2,4-triazol-1-yl)-propan-2-ol of the formula

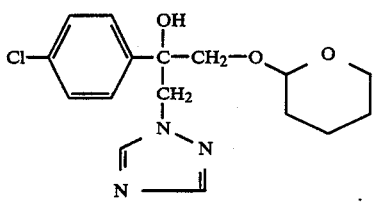

or an addition product thereof with an acid or metal salt.

6. A compound according to claim 1, wherein such compound is 2-(2,4-dichlorophenyl)-1-[(tetrahydro-2H-pyran-2-yl)-oxy]-3-(1,2,4-triazol-1-yl)-propan-2-ol of the formula

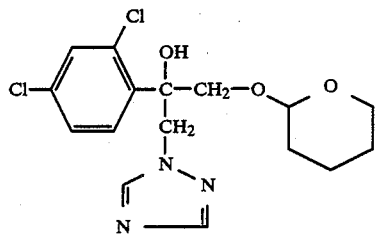

or an addition product thereof with an acid or metal salt.

7. A fungicidal and plant growth-regulating composition comprising an amount effective therefor of a compound or addition product according to claim 1 and an inert diluent.

8. A method of combating fungi which comprises applying to such fungi or to a fungus habitat an amount effective therefor of a compound or addition product according to claim 1.

9. The method according to claim 8, wherein such compound is
2-tert.-butyl-1-[(tetrahydro-2H-pyran-2-yl)-oxy]-3-(1,2,4-triazol-1-yl)-propan-2-ol, 2-(4-chlorophenyl)-1-[(tetrahydro-2H-pyran-2-yl)-oxy]-3-(1,2,4-triazol-1-yl)-propan-2-ol, or 2-2,4-dichlorophenyl)-1-[(tetrahydro-2H-pyran-2-yl)-oxy]-3-(1,2,4-triazol-1-yl)-propan-2-ol,
or an addition product thereof with an acid or metal salt.

10. A method of regulating the growth of plants which comprises applying to such plants or to a locus in which such plants are growing or are to be grown an amount effective therefor of a compound or addition product according to claim 1.

11. The method according to claim 10, wherein such compound is
2-tert.-butyl-1-[(tetrahydro-2H-pyran-2-yl)-oxy]-3-(1,2,4-triazol-1-yl)-propan-2-ol,
2-(4-chlorophenyl)-1-[(tetrahydro-2H-pyran-2-yl)-oxy]-3-(1,2,4-triazol-1-yl)-propan-2-ol, or
2-(2,4-dichlorophenyl)-1-[(tetrahydro-2H-pyran-2-yl)-oxy]-3-(1,2,4-triazol-1-yl)-propan-2-ol,
or an addition product thereof with an acid or metal salt.

* * * * *